(12) United States Patent
Buettelmann et al.

(10) Patent No.: US 7,544,704 B2
(45) Date of Patent: Jun. 9, 2009

(54) ARYL-4-ETHYNYL-ISOXAZOLE DERIVATIVES

(75) Inventors: Bernd Buettelmann, Schopfheim (DE); Henner Knust, Rheinfelden (DE); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 197 days.

(21) Appl. No.: 11/805,640

(22) Filed: May 24, 2007

(65) Prior Publication Data
US 2007/0287739 A1 Dec. 13, 2007

(30) Foreign Application Priority Data
May 31, 2006 (EP) .................................. 06114745

(51) Int. Cl.
- A61K 31/44 (2006.01)
- A61K 31/42 (2006.01)
- C07D 261/06 (2006.01)
- C07D 413/06 (2006.01)

(52) U.S. Cl. ....................... 514/340; 544/224; 544/336; 546/268.1; 546/268.4; 546/272.1; 548/240; 514/252.1; 514/378

(58) Field of Classification Search .................. 544/224, 544/336; 546/268.1, 268.4, 272.1; 548/240; 514/252.1, 336, 340, 378
See application file for complete search history.

(56) References Cited

U.S. PATENT DOCUMENTS

| 4,639,266 A | 1/1987 | Heubach et al. |
| 2003/0055085 A1 | 3/2003 | Wagener et al. |
| 2004/0006226 A1 | 1/2004 | Ladduwahetty et al. |

FOREIGN PATENT DOCUMENTS

| DE | 3525205 | 3/1986 |
| GB | 2336589 | 10/1999 |
| WO | WO 01/29015 | 4/2001 |
| WO | WO 01/34603 | 5/2001 |
| WO | WO 02/50062 A2 | 6/2002 |
| WO | WO 02/081474 A1 | 10/2002 |
| WO | WO 03/004027 | 1/2003 |
| WO | WO 03/044017 | 5/2003 |
| WO | WO 2005/014553 | 2/2005 |
| WO | WO 2005/118568 | 12/2005 |
| WO | WO 2005/123672 A2 | 12/2005 |
| WO | WO 2006/044617 | 4/2006 |
| WO | WO 2006/069155 | 6/2006 |

OTHER PUBLICATIONS

Frolund, B., et al., European Journal of Medicinal Chemistry, vol. 38, No. 4, pp. 447-449 (2003), XP004425020.
Frolund, B., et al., Journal of Medicinal Chemistry, vol. 45, No. 12, pp. 2454-2468 (2002), XP002303063.
Turbanova, E.S., et al., Zhurnal Organicheskoi Khimii, vol. 19(1), pp. 221-222 (1983), XP009088724.
McNamara et al., Psychobiology (1993), vol. 21, pp. 101-108.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Burke, et al., Journal of Natural Products, 1986, vol. 49, pp. 522-523.
Hamper et al., J. Agric. Food Chem. (1995), vol. 43, pp. 219-228.
Kumar, et al., Tetrahedron Letters, vol. 47, (2006), p. 1457-1460.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).
Austin et al., J. Org. Chem. vol. 46, pp. 2280-2286 (1981).
Schlosser et al., Eur. J. Org. Chem. vol. (24), p. 4181-4184 (2002).
Hüttel et al., Liebigs, Ann. Chem. vol. 593, pp. 200-207 (1955) (English translation).
Seydel et al., J. Med. Chem. vol. (19) pp. 483-492 (1976).
Kirk, K. L., J. Org. Chem. vol. (43) pp. 4381-4383 (1978).

*Primary Examiner*—Golam M Shameem
(74) *Attorney, Agent, or Firm*—George W. Johnston; Patricia S. Rocha-Tramaloni; Kimberly J. Prior

(57) ABSTRACT

The present invention is concerned with aryl-4-ethynyl-isoxazole derivatives of formula I

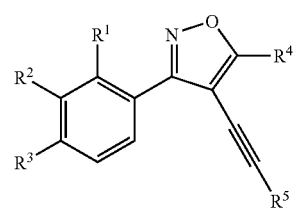

wherein $R^1$ to $R^5$ are as described in the specification and pharmaceutically acceptable salt thereof. This class of compounds has high affinity and selectivity for GABA A α5 receptor binding sites, being useful as a cognitive enhancer or for the treatment of cognitive disorders like Alzheimer's disease.

28 Claims, No Drawings

ARYL-4-ETHYNYL-ISOXAZOLE DERIVATIVES

PRIORITY TO RELATED APPLICATION(S)

This application claims the benefit of European Patent Application No. 06114745.0, filed May 31, 2006, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel super family and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhance spatial learning in the Morris water maze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides aryl-4-ethynyl-isoxazole derivatives of formula I

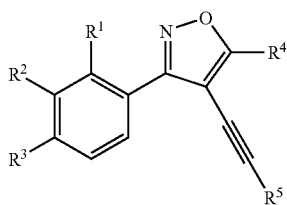

wherein
$R^1$, $R^2$, and $R^3$ are each independently hydrogen, lower alkyl, halogen, lower alkoxy or amino;
$R^4$ is lower alkyl;
$R^5$ is optionally substituted aryl or heteroaryl, wherein the substituents are selected from the group consisting of lower alkyl, lower alkoxy, $CF_3$, halogen, hydroxy, amino, —$(CH_2)_n$—CN, —C(O)O-lower alkyl, —$S(O)_2NH_2$, —C(O)—NH—$(CH_2)_n$-cycloalkyl, —C(O)—NH-heterocyclyl, —C(O)—NH-heteroaryl, and optionally substituted aryl, wherein the substituents are selected from halogen;
n is 0 or 1;

and pharmaceutically acceptable acid addition salts thereof.

The invention also provides pharmaceutical compositions comprising a therapeutically acceptable amount of a compound of formula I and a pharmaceutically acceptable carrier. The invention further provides methods for the manufacture of compounds and compositions of the invention.

Compounds of the invention have high affinity and selectivity for GABA A α5 receptor binding sites and might be useful as a cognitive enhancer or for the treatment of cognitive disorders like Alzheimer's disease. The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-7, preferably from 1-4, carbon atoms, for example, methyl, ethyl, propyl, isopropyl, n-butyl, i-butyl, t-butyl and the like.

As used herein, the term "lower alkoxy" denotes a straight- or branched-chain alkyl group as defined above which is attached via an oxygen atom.

The term "heterocyclyl" denotes a saturated carbon ring having 5 to 6 ring atoms, containing one or more heteroatoms, selected from O, N and S. Examples for such group are tetrahydropyran-4-yl or piperidin-4-yl.

The term "aryl" denotes an unsaturated 5 or 6 membered carbon ring, for example a phenyl, benzyl or naphthyl group. A preferred aryl group is phenyl.

The term "halogen" denotes chlorine, iodine, fluorine and bromine.

The term "cycloalkyl" denotes a cyclic hydrocarbon ring, having from 3 to 7 carbon ring atoms, for example, cyclopropyl, cyclopentyl or cyclohexyl.

The term "heteroaryl" denotes an aromatic 5 or 6 membered ring containing from one to three heteroatoms, selected from N, O and S atoms. Examples of such aromatic heteroaryl rings are furan, pyridine, pyrimidine, pyridazine, isoxazole, imidazole, pyrazole, thiazole, pyrazine, quinoxaline, 4H-5-oxa-2,9b-diaza-cyclopenta[a]naphthalene, 5,6,7,8-tetrahydro-imidazo[1,2-a]pyridine, triazole or thiophen.

The term "optionally substituted aryl or heteroaryl" means that the aryl or heteroaryl can be unsubstituted or substituted by one or more substituents, preferably by one to three substituents.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides aryl-4-ethynyl-isoxazole derivatives of formula I

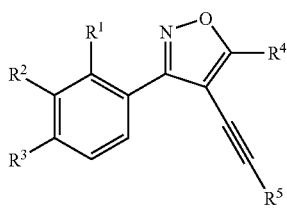

I wherein
$R^1$, $R^2$, and $R^3$ are each independently hydrogen, lower alkyl, halogen, lower alkoxy or amino;
$R^4$ is lower alkyl;
$R^5$ is optionally substituted aryl or heteroaryl, wherein the substituents are selected from the group consisting of lower alkyl, lower alkoxy, $CF_3$, halogen, hydroxy, amino, —$(CH_2)_n$—CN, —C(O)O-lower alkyl, —$S(O)_2NH_2$, —C(O)—NH—$(CH_2)_n$-cycloalkyl, —C(O)—NH-heterocyclyl, —C(O)—NH-heteroaryl, and optionally substituted aryl, wherein the substituents are selected from halogen;
n is 0 or 1;

and pharmaceutically acceptable acid addition salts thereof.

Exemplary preferred are compounds that have a binding activity (hKi) of lower than 100 nM and are selective for GABA A α5 subunits and are relatively free of activity at GABA A α1, α2 and α3 receptor binding sites.

In a certain embodiment, $R^1$, $R^2$, and $R^3$ are all hydrogen.

In a certain embodiment, $R^1$, $R^2$, and $R^3$ are each independently hydrogen, halogen or lower alkoxy. Of these compounds, in certain embodiments $R^2$ is halogen, in particular chlorine. Also of these compounds, in certain embodiments $R^3$ is alkoxy, in particular methoxy.

In a certain embodiment, $R^1$ is hydrogen, $R^2$ is hydrogen or halogen and $R^3$ is hydrogen, lower alkoxy or halogen.

In a certain embodiment, $R^4$ is methyl.

In a certain embodiment, $R^5$ is optionally substituted aryl or heteroaryl, wherein the substituents are selected from the groups consisting of lower alkyl, lower alkoxy, $CF_3$, halogen, hydroxy, amino, CN, —$CH_2CN$, —C(O)O-lower alkyl, —$S(O)_2NH_2$, —C(O)—NH—$CH_2$-cycloalkyl, —C(O)—NH-heterocyclyl, —C(O)—NH-heteroaryl, optionally substituted aryl, wherein the substituents are selected from halogen.

Preferred compounds of formula I are those, in which $R^5$ is optionally substituted pyridinyl, and the other substituents are as described above, for example the following compounds
2-(5-methyl-3-phenyl-isoxazol-4-ylethynyl)-pyridine,
2-(5-methyl-3-phenyl-isoxazol-4-ylethynyl)-isonicotinic acid methyl ester,
N-cyclopropylmethyl-2-(5-methyl-3-phenyl-isoxazol-4-ylethynyl)-isonicotinamide,
2-(5-methyl-3-phenyl-isoxazol-4-ylethynyl)-N-(tetrahydro-pyran-4-yl)-isonicotinamide,
2-(5-methyl-3-phenyl-isoxazol-4-ylethynyl)-N-(4-methyl-thiazol-2-yl)-isonicotinamide,
2-chloro-6-(5-methyl-3-phenyl-isoxazol-4-ylethynyl)-pyridine,
5-methyl-2-(5-methyl-3-phenyl-isoxazol-4-ylethynyl)-pyridine,
2-methyl-6-(5-methyl-3-phenyl-isoxazol-4-ylethynyl)-pyridine,
4-methyl-2-(5-methyl-3-phenyl-isoxazol-4-ylethynyl)-pyridine,
2-(5-methyl-3-phenyl-isoxazol-4-ylethynyl)-4-trifluoromethyl-pyridine,
3-methyl-2-(5-methyl-3-phenyl-isoxazol-4-ylethynyl)-pyridine,
6-(5-methyl-3-phenyl-isoxazol-4-ylethynyl)-pyridin-3-ylamine,
5-chloro-2-(5-methyl-3-phenyl-isoxazol-4-ylethynyl)-pyridine and
4-ethyl-2-(5-methyl-3-phenyl-isoxazol-4-ylethynyl)-pyridine.

Also preferred is 2-[3-(4-chloro-phenyl)-5-methyl-isoxazol-4-ylethynyl]-pyridine.

Preferred compounds of formula I are further those, in which $R^5$ is optionally substituted phenyl, and the other substituents are as described above, for example the following compounds
3-(5-methyl-3-phenyl-isoxazol-4-ylethynyl)-N-(tetrahydro-pyran-4-yl)-benzamide,
2-(5-methyl-3-phenyl-isoxazol-4-ylethynyl)-benzoic acid methyl ester and
2-(5-methyl-3-phenyl-isoxazol-4-ylethynyl)-phenylamine.

Preferred compounds of formula I are further those, in which $R^5$ is optionally substituted pyridazine, and the other substituents are as described above, for example the following compound
3-methyl-6-(5-methyl-3-phenyl-isoxazol-4-ylethynyl)-pyridazine.

Preferred compounds of formula I are further those, in which $R^5$ is optionally substituted imidazole, and the other substituents are as described above, for example the following compounds
5-methyl-4-(1-methyl-1H-imidazol-2-ylethynyl)-3-phenyl-isoxazole,
5-methyl-4-(2-methyl-3H-imidazol-4-ylethynyl)-3-phenyl-isoxazole,
4-(1H-imidazol-2-ylethynyl)-5-methyl-3-phenyl-isoxazole,
5-methyl-4-(1-methyl-5-phenyl-1H-imidazol-2-ylethynyl)-3-phenyl-isoxazole,
5-methyl-4-(5-methyl-1-phenyl-1H-imidazol-2-ylethynyl)-3-phenyl-isoxazole,
3,5-dimethyl-2-(5-methyl-3-phenyl-isoxazol-4-ylethynyl)-3H-imidazole-4-carboxylic acid ethyl ester,
4-[1-(3,5-difluoro-phenyl)-2,5-dimethyl-1H-imidazol-4-ylethynyl]-5-methyl-3-phenyl-isoxazole and
4-[1-(4-fluoro-phenyl)-2,5-dimethyl-1H-imidazol-4-ylethynyl]-5-methyl-3-phenyl-isoxazole.

Preferred compounds of formula I are further those, in which R⁵ is optionally substituted pyrazole, and the other substituents are as described above, for example the following compounds
5-methyl-4-(4-methyl-1H-pyrazol-3-ylethynyl)-3-phenyl-isoxazole,
4-[5-(4-fluoro-phenyl)-1-methyl-1H-pyrazol-3-ylethynyl]-5-methyl-3-phenyl-isoxazole and
4-[5-(3-fluoro-phenyl)-1-methyl-1H-pyrazol-3-ylethynyl]-5-methyl-3-phenyl-isoxazole.

Preferred compounds of formula I are further those, in which R⁵ is optionally substituted thiazole, and the other substituents are as described above, for example the following compounds
2-methyl-5-(5-methyl-3-phenyl-isoxazol-4-ylethynyl)-thiazole-4-carboxylic acid ethyl ester,
2-(5-methyl-3-phenyl-isoxazol-4-ylethynyl)-thiazole-5-carboxylic acid methyl ester, and
2-(5-methyl-3-phenyl-isoxazol-4-ylethynyl)-thiazole-4-carboxylic acid methyl ester.

Preferred compounds of formula I are further those, in which R⁵ is optionally substituted pyrazine, and the other substituents are as described above, for example the following compounds
2,5-dimethyl-3-(5-methyl-3-phenyl-isoxazol-4-ylethynyl)-pyrazine,
2-(5-methyl-3-phenyl-isoxazol-4-ylethynyl)-pyrazine,
6-(5-methyl-3-phenyl-isoxazol-4-ylethynyl)-pyrazin-2-ylamine and
5-(5-methyl-3-phenyl-isoxazol-4-ylethynyl)-pyrazin-2-ylamine.

Preferred compounds of formula I are further those, in which R⁵ is optionally substituted quinoxaline, and the other substituents are as described above, for example the following compound
2-(5-methyl-3-phenyl-isoxazol-4-ylethynyl)-quinoxaline.

Preferred compounds of formula I are further those, in which R⁵ is optionally substituted 5,5,7,8-tetrahydro-imidazo[1,2-a]pyridine, and the other substituents are as described below, for example the following compound
3-methyl-2-(5-methyl-3-phenyl-isoxazol-4-ylethynyl)-5,6,7,8-tetrahydro-imidazo[1,2-a]pyridine.

The present compounds of formula I and their pharmaceutically acceptable salts can be prepared by methods known in the art, for example, by processes described below.

The present compounds of formula I and their pharmaceutically acceptable salts can be prepared by methods known in the art, for example, by processes described below, which process comprises
a) reacting a compound of formula II

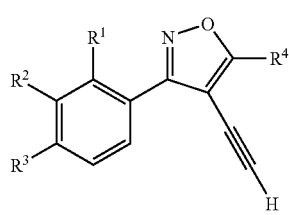

II with a compound of formula III

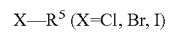

III in the presence of a palladium(0)-catalyst, copper(I) salt and a base to give a compound of formula

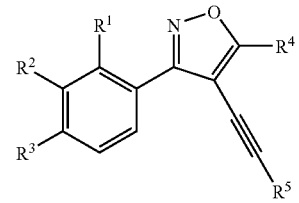

I wherein R¹, R², R³, R⁴ and R⁵ are as described above, or
b) reacting a compound of formula II

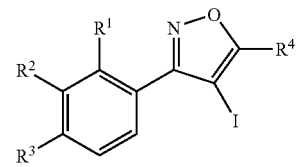

IV with a compound of formula V

V in the presence of a palladium(0)-catalyst, copper(I) salt and a base to give a compound of formula

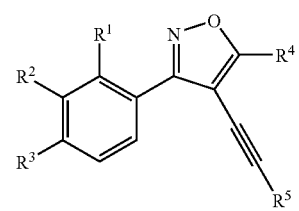

I wherein R¹, R², R³, R⁴ and R⁵ are as described above, and, if desired, converting a compound of formula I into a pharmaceutically acceptable salt.

The following schemes describe the processes for preparation of compounds of formula I in more detail. The starting materials of formulas III, IV and VI are known compounds or may be prepared according to methods known in the art.

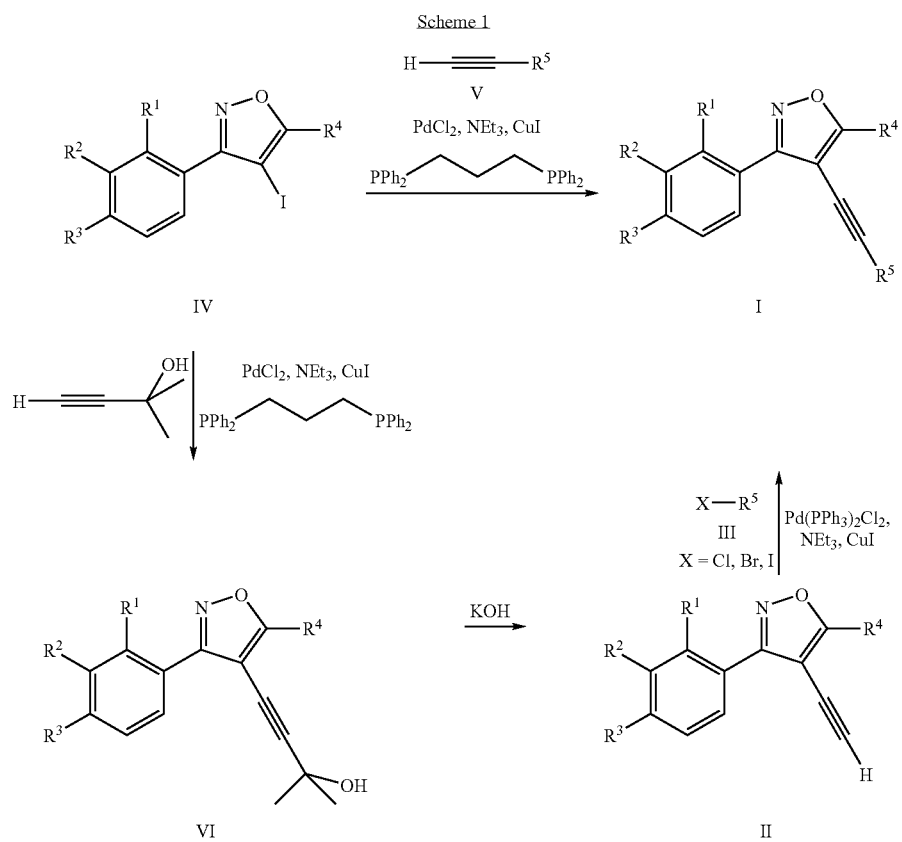

Scheme 1

In accordance with scheme 1, a compound of formula I can be prepared starting from iodide IV (Org. Lett. (17) 5203, 2005) in a Sonogashira-type coupling reaction using a palladium-catalyst like palladium(II) chloride, a ligand like 1,3-bis(diphenylphosphino)propane, a base like triethylamine and a copper(I) source like copper iodide with a corresponding ethynyl-compound of formula V in a suitable solvent like DMF at ambient or elevated temperature. Alternatively, in a corresponding Sonogashira-type coupling reaction a suitable ethynyl-compound like 2-methyl-but-3-yn-2-ol can be used to afford compound VI which can be transformed by treatment with a base like potassium hydroxide in a suitable solvent like toluene at ambient or elevated temperature to provide the ethynyl-isoxazole compound of formula II. Compounds of formula I can be prepared starting from compounds of formula II in a similar Sonogashira-type coupling reaction with a corresponding aryl- or heteroarylhalide of formula III.

As mentioned earlier, the compounds of formula I and their pharmaceutically acceptable salts possess valuable pharmacological properties. Compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2, α3 subunits and 0.5 nM for a5 subunits and the test compound in the range of $10-10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and all were found to possess a Ki value for displacement of [3H]flumazenil from a5 subunits of the rat GABA A receptor of 100 nM or less. In a preferred embodiment the compounds of the invention are binding selective for the α5 subunit relative to the α1, α2 and α3 subunit.

| Example No. | Ki[nM] hα5 |
|---|---|
| 1 | 47.9 |
| 8 | 91.6 |
| 12 | 87.3 |
| 14 | 38.4 |
| 17 | 74.9 |
| 19 | 26.6 |
| 21 | 26.0 |
| 22 | 77.2 |
| 23 | 53.0 |
| 24 | 85.2 |
| 26 | 10.4 |
| 27 | 39.8 |
| 28 | 20.7 |
| 29 | 90.1 |
| 30 | 71.9 |
| 31 | 45.5 |
| 32 | 28.4 |
| 33 | 23.7 |
| 34 | 59.2 |
| 35 | 39.3 |
| 37 | 48.0 |
| 38 | 37.0 |
| 39 | 28.9 |
| 41 | 55.7 |
| 42 | 81.7 |
| 44 | 38.9 |
| 45 | 84.4 |
| 46 | 18.3 |
| 47 | 37.2 |
| 50 | 7.3 |
| 52 | 15.5 |
| 53 | 52.6 |
| 56 | 23.5 |
| 57 | 39.1 |
| 59 | 54.5 |
| 61 | 31.9 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compounds of the invention have high affinity and selectivity for GABA A α5 receptor binding sites and might be useful as a cognitive enhancer or for the treatment of cognitive disorders like Alzheimer's disease. The invention provides a method for enhancing cognition which comprises administering to an individual a therapeutically effective amount of a compound of formula I or a pharmaceutically acceptable salt thereof. The invention also provides a method for treating Alzheimer's disease which comprises administering to an individual a therapeutically effective amount of a compound of formula I or a pharmaceutically acceptable salt thereof.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1-51 are provided for illustration of the invention. They should not be considered as limiting the scope of the invention, but merely as being representative thereof. Example 1 has been described in detail, the remaining compounds have been prepared accordingly.

EXAMPLE 1

2-(5-Methyl-3-phenyl-isoxazol-4-ylethynyl)-pyridine

A mixture of 4-iodo-5-methyl-3-phenylisoxazole (285 mg, 1.00 mmol), palladium(II) acetate (7 mg, 0.03 mmol), 1,3-bis(diphenylphosphino)propane (12 mg, 0.03 mmol), triethylamine (348 µL, 2.50 mmol) and 2-ethynylpyridine (131 µL, 1.30 mmol) in N,N-dimethylformamide (2 mL) was evaporated and flushed with argon. Cuprous iodide (4 mg, 0.02 mmol) was added and the reaction mixture was stirred for 3 h at 90° C. before cooling to ambient temperature and separated between aqueous sodium hydroxide (1 M, 30 mL) and ethyl acetate (50 mL). The aqueous layer was extracted with ethyl acetate (50 mL) and washed with aqueous sodium hydroxide (1 M, 30 mL). The combined organic layers were dried over sodium sulfate and concentrated. Purification by chromatography ($SiO_2$, heptane:ethyl acetate=100:0 to 67:33) afforded the title compound (60 mg, 23%) as a light brown solid. MS: m/e=261.2 $[M+H]^+$.

EXAMPLE 2

3-(5-Methyl-3-phenyl-isoxazol-4-ylethynyl)-pyridine

As described for example 1,4-iodo-5-methyl-3-phenylisoxazole (285 mg, 1.00 mmol) was converted (using 3-ethynylpyridine instead of 2-ethynylpyridine) to the title compound ($SiO_2$, heptane:ethyl acetate=100:0 to 67:33, 150 mg, 58%) which was obtained as a white solid. MS: m/e=261.2 $[M+H]^+$.

EXAMPLE 3

5-(5-Methyl-3-phenyl-isoxazol-4-ylethynyl)-pyridin-2-ylamine a) 5-Trimethylsilanylethynyl-pyridin-2-ylamine A mixture of 2-amino-5-bromopyridine (50.0 g, 289 mmol), trimethylsilylacetylene (112 mL, 809 mmol), triethylamine (120 mL, 867 mmol), $PdCl_2(PPh_3)_2$ (4.06 g, 5.78 mmol) and $PPh_3$ (1.52 g, 5.78 mmol) in DMF (290 mL) was purged for 10 min with argon. Then cuprous iodide (340 mg, 2.89 mmol) was added and the reaction mixture was heated up to 90° C., stirring was continued at 90° C. for 4.5 h. Cooled to ambient temperature, the reaction mixture was concentrated, poured onto water (300 mL) and extracted with ethyl acetate (3×500 mL). The combined organic layers were washed with water (300 mL) and brine (2×250 mL) and dried over magnesium sulfate. Concentration left a dark brown residue which was purified by flash chromatography with n-heptane and acetone to give the title compound as a brown solid (41.7 g, 76%). MS: m/e=191.2 $[M+H]^+$.

b) 5-Ethynyl-pyridin-2-ylamine

To a solution of 5-trimethylsilanylethynyl-pyridin-2-ylamine (32.1 g, 169 mmol) in THF (150 mL) and methanol (350 mL) at 0° C. was added potassium carbonate (2.33 g, 16.9 mmol) and the mixture was stirred at 0° C. for 5 h. It was diluted with ice water (500 mL), extracted with tert-butylmethylether (3×500 mL), washed the combined organic layers with brine and dried over magnesium sulfate. Concentration left a dark brown solid, which was dissolved in hot ethyl acetate and precipitated with n-heptane trituration to give the 5-ethynyl-pyridin-2-ylamine (14.61 g, 73%) as a light brown solid. MS: m/e=118.1 $[M+H]^+$.

c) 5-(5-Methyl-3-phenyl-isoxazol-4-ylethynyl)-pyridin-2-ylamine

As described for example 1,4-iodo-5-methyl-3-phenylisoxazole (285 mg, 1.00 mmol) was converted (using 5-ethynyl-pyridin-2-ylamine instead of 2-ethynylpyridine) to the title compound ($SiO_2$, heptane:ethyl acetate=100:0 to 67:33, 158 mg, 57%) which was obtained as a light yellow solid. MS: m/e=276.2 $[M+H]^+$.

EXAMPLE 4

4-(5-Methyl-3-phenyl-isoxazol-4-ylethynyl)-benzonitrile

As described for example 1,4-iodo-5-methyl-3-phenylisoxazole (285 mg, 1.00 mmol) was converted (using 4-ethynyl-benzonitrile instead of 2-ethynylpyridine) to the title compound ($SiO_2$, heptane:ethyl acetate=100:0 to 67:33, 60 mg, 21%) which was obtained as a white solid. MS: m/e=285.1 $[M+H]^+$.

EXAMPLE 5

3-(5-Methyl-3-phenyl-isoxazol-4-ylethynyl)-benzoic acid methyl ester

As described for example 1,4-iodo-5-methyl-3-phenylisoxazole (1.14 g, 4.00 mmol) was converted [using 3-ethynyl-benzoic acid methyl ester (prepared according to J. Org. Chem. 46(11), 2280, 1981) instead of 2-ethynylpyridine] to the title compound ($SiO_2$, heptane:ethyl acetate=100:0 to 90:10, 0.67 g, 53%) which was obtained as a light yellow solid. MS: m/e=318.1 [M+H]+.

EXAMPLE 6

4-(5-Methyl-3-phenyl-isoxazol-4-ylethynyl)-benzoic acid methyl ester

As described for example 1,4-iodo-5-methyl-3-phenyl-isoxazole (1.14 g, 4.00 mmol) was converted [using 4-ethynyl-benzoic acid methyl ester (prepared according to J. Org. Chem. 68(12), 4862, 2003) instead of 2-ethynylpyridine] to the title compound (SiO$_2$, heptane:ethyl acetate=100:0 to 90:10, 0.66 g, 52%) which was obtained as a light yellow solid. MS: m/e=318.1 [M+H]+.

EXAMPLE 7

N-Cyclopropylmethyl-3-(5-methyl-3-phenyl-isoxazol-4-ylethynyl)-benzamide a) 3-(5-Methyl-3-phenyl-isoxazol-4-ylethynyl)-benzoic acid 3-(5-Methyl-3-phenyl-isoxazol-4-ylethynyl)-benzoic acid methyl ester (600 mg, 1.89 mmol) was treated with ethanol (12 mL) and aqueous sodium hydroxide (1 M, 7.56 mL, 7.56 mmol). The reaction mixture was heated for 1.5 h at 80° C. After concentration and dilution with water (9 mL) the pH was adjusted to 1.5 by adding hydrochloric acid (1 M, 8 mL). The resulting suspension was stirred for 30 min at 0° C. and filtered. Washing with ice-cold water (10 mL) and drying afforded the title compound (546 mg, 95%) as a light brown solid. MS: m/e=304.1 [M+H]+.

b) N-Cyclopropylmethyl-3-(5-methyl-3-phenyl-isoxazol-4-ylethynyl)-benzamide To a solution of 3-(5-methyl-3-phenyl-isoxazol-4-ylethynyl)-benzoic acid (250 mg; 0.82 mmol) in N,N-dimethylformamide (4.8 mL) was added 2-(1H-benzotriazole-1-yl)-1,1,3,3-tetramethyluronium tetrafluoroborate (318 mg, 0.99 mmol) at 0° C. After stirring for 15 min at this temperature, aminomethylcyclopropane (86 µl, 0.99 mmol) and N-ethyldiisopropylamine (0.85 mL, 4.94 mmol) were added and the reaction mixture was allowed to warm to ambient temperature. After 1.75 h stirring at ambient temperature, it was extracted with dichloromethane (300 mL) and aqueous sodium carbonate (2 M, 75 mL). The combined organic layers were washed with brine (75 mL), dried over sodium sulfate and concentrated. Purification by chromatography (SiO$_2$, heptane:ethyl acetate=95:5 to 0:100) afforded the title compound (254 mg, 87%) as a white solid. MS: m/e=357.1 [M+H]+.

EXAMPLE 8

3-(5-Methyl-3-phenyl-isoxazol-4-ylethynyl)-N-(tetrahydro-pyran-4-yl)-benzamide As described for example 7b, 3-(5-methyl-3-phenyl-isoxazol-4-ylethynyl)-benzoic acid (250 mg; 0.82 mmol) was converted (using 4-amino-tetrahydropyrane instead of aminomethylcyclopropane) to the title compound (SiO$_2$, heptane:ethyl acetate=95:5 to 0:100, 276 mg, 87%) which was obtained as a white solid. MS: m/e=387.1 [M+H]+.

EXAMPLE 9

N-Cyclopropylmethyl-4-(5-methyl-3-phenyl-isoxazol-4-ylethynyl)-benzamide a) 4-(5-Methyl-3-phenyl-isoxazol-4-ylethynyl)-benzoic acid

As described for example 7a, 4-(5-methyl-3-phenyl-isoxazol-4-ylethynyl)-benzoic acid methyl ester (600 mg, 1.89 mmol) instead of 3-(5-methyl-3-phenyl-isoxazol-4-ylethynyl)-benzoic acid methyl ester was converted to the title compound (549 mg, 96%) which was obtained as an off-white solid. MS: m/e=304.1 [M+H]+.

b) N-Cyclopropylmethyl-4-(5-methyl-3-phenyl-isoxazol-4-ylethynyl)-benzamide As described for example 7b, 4-(5-methyl-3-phenyl-isoxazol-4-ylethynyl)-benzoic acid (250 mg; 0.82 mmol) instead of 3-(5-methyl-3-phenyl-isoxazol-4-ylethynyl)-benzoic acid was converted to the title compound (SiO$_2$, heptane:ethyl acetate=95:5 to 0:100, 108 mg, 39%) which was obtained as a light yellow solid. MS: m/e=357.1 [M+H]+.

EXAMPLE 10

4-(5-Methyl-3-phenyl-isoxazol-4-ylethynyl)-N-(tetrahydro-pyran-4-yl)-benzamide As described for example 7b, 4-(5-methyl-3-phenyl-isoxazol-4-ylethynyl)-benzoic acid (250 mg; 0.82 mmol) instead of 3-(5-methyl-3-phenyl-isoxazol-4-ylethynyl)-benzoic acid was converted using 4-amino-tetrahydropyrane instead of aminomethylcyclopropane to the title compound (SiO$_2$, heptane:ethyl acetate=95:5 to 0:100, 281 mg, 88%) which was obtained as a white solid. MS: m/e=387.1 [M+H]+.

EXAMPLE 11

2-Chloro-4-(5-methyl-3-phenyl-isoxazol-4-ylethynyl)-pyridine a) 2-Methyl-4-(5-methyl-3-phenyl-isoxazol-4-yl)-but-3-yn-2-ol

A mixture of 4-iodo-5-methyl-3-phenylisoxazole (5.73 g, 20.1 mmol), palladium(II) acetate (135 mg, 0.60 mmol), 1,3-bis(diphenylphosphino)propane (249 mg, 0.60 mmol), triethylamine (7.0 mL, 50.2 mmol) and 2-methyl-3-butyn-2-ol (3.0 mL, 30.7 mmol) in N,N-dimethylformamide (40 mL) was evaporated and flushed with argon. Cuprous iodide (77 mg, 0.40 mmol) was added and the reaction mixture was stirred for 23 h at 90° C. (after 1.75 h and 4.5 h, respectively, further palladium(II) acetate (135 mg, 0.60 mmol), 1,3-bis(diphenylphosphino)propane (249 mg, 0.60 mmol), triethylamine (7.0 mL, 50.2 mmol), 2-methyl-3-butyn-2-ol (3.0 mL, 30.7 mmol) and cuprous iodide (77 mg, 0.40 mmol) were added) before cooled to ambient temperature and separated between aqueous sodium hydroxide (1 M, 600 mL) and ethyl acetate (1000 mL). The aqueous layer was extracted with ethyl acetate (1000 mL) and washed with aqueous sodium hydroxide (1 M, 600 mL). The combined organic layers were dried over sodium sulfate and concentrated. Purification by chromatography (SiO$_2$, heptane:ethyl acetate=67:33) afforded the title compound (3.77 g, 78%) as a yellow oil. MS: m/e=242.2 [M+H]+.

b) 4-Ethynyl-5-methyl-3-phenyl-isoxazole

To a solution of 2-methyl-4-(5-methyl-3-phenyl-isoxazol-4-yl)-but-3-yn-2-ol (3.77 g, 15.6 mmol) in toluene (38 mL) was added potassium hydroxide (350 mg, 6.24 mmol) and the reaction mixture was stirred for 1.25 h at 110° C. before being cooled to ambient temperature and separated between ethyl acetate (500 mL) and aqueous ammonium chloride (1 M, 400 mL). The aqueous layer was extracted with ethyl acetate (500 mL) and the combined organic layers were dried over sodium sulfate and concentrated. Purification by chromatography ($SiO_2$, heptane:ethyl acetate=100:0 to 90:10) afforded the title compound (2.50 g, 87%) as a yellow solid. MS: m/e=184.1 $[M+H]^+$.

c) 2-Chloro-4-(5-methyl-3-phenyl-isoxazol-4-ylethynyl)-pyridine

A mixture of 4-ethynyl-5-methyl-3-phenyl-isoxazole (110 mg, 0.60 mmol), 2-chloro-4-iodopyridine (172 mg, 0.72 mmol), triethylamine (209 µl, 1.50 mmol) and bis(triphenylphosphine)palladium(II) chloride (13 mg, 0.02 mmol) in N,N-dimethylformamide (1.2 mL) was evaporated and flushed with argon. Cuprous iodide (2 mg, 0.01 mmol) was added and the reaction mixture was stirred for 1.5 h at 90° C. before it was cooled to ambient temperature and separated between aqueous sodium hydroxide (1 M, 20 mL) and ethyl acetate (30 mL). The aqueous layer was extracted with ethyl acetate (30 mL) and the combined organic layers were washed with aqueous sodium hydroxide (1 M, 20 mL), dried over sodium sulfate and concentrated. Purification by chromatography ($SiO_2$, heptane:ethyl acetate=100:0 to 80:20) afforded the title compound (160 mg, 91%) as a colorless oil. MS: m/e=295.0/297.2 $[M+H]^+$.

EXAMPLE 12

2-(5-Methyl-3-phenyl-isoxazol-4-ylethynyl)-benzoic acid methyl ester

As described for example 11c, 4-ethynyl-5-methyl-3-phenyl-isoxazole (110 mg, 0.60 mmol) was converted (using methyl 2-iodobenzoate instead of 2-chloro-4-iodopyridine) to the title compound ($SiO_2$, heptane:ethyl acetate=100:0 to 80:20, 166 mg, 82%) which was obtained as an off-white solid. MS: m/e=318.1 $[M+H]^+$.

EXAMPLE 13

2-(5-Methyl-3-phenyl-isoxazol-4-ylethynyl)-pyridin-3-ol

As described for example 11c, 4-ethynyl-5-methyl-3-phenyl-isoxazole (110 mg, 0.60 mmol) was converted (using 2-iodo-3-hydroxypyridine instead of 2-chloro-4-iodopyridine) to the title compound ($SiO_2$, heptane:ethyl acetate=95:5 to 50:50, 93 mg, 56%) which was obtained as a light yellow solid. MS: m/e=377.1 $[M+H]^+$.

EXAMPLE 14

2-(5-Methyl-3-phenyl-isoxazol-4-ylethynyl)-phenylamine

As described for example 11c, 4-ethynyl-5-methyl-3-phenyl-isoxazole (110 mg, 0.60 mmol) was converted (using 2-iodo-aniline instead of 2-chloro-4-iodopyridine) to the title compound ($SiO_2$, heptane:ethyl acetate=100:0 to 50:50, 139 mg, 85%) which was obtained as a light brown oil. MS: m/e=375.1 $[M+H]^+$.

EXAMPLE 15

[2-(5-Methyl-3-phenyl-isoxazol-4-ylethynyl)-phenyl]-acetonitrile

As described for example 11c, 4-ethynyl-5-methyl-3-phenyl-isoxazole (110 mg, 0.60 mmol) was converted (using 2-iodo-phenylacetonitrile instead of 2-chloro-4-iodopyridine) to the title compound ($SiO_2$, heptane:ethyl acetate=100:0 to 80:20, 156 mg, 87%) which was obtained as a light brown oil. MS: m/e=375.1 $[M+H]^+$.

EXAMPLE 16

N-Cyclopropylmethyl-2-(5-methyl-3-phenyl-isoxazol-4-ylethynyl)-benzamide a) 2-(5-Methyl-3-phenyl-isoxazol-4-ylethynyl)-benzoic acid

As described for example 7a, 2-(5-methyl-3-phenyl-isoxazol-4-ylethynyl)-benzoic acid methyl ester (100 mg, 0.32 mmol) instead of 3-(5-methyl-3-phenyl-isoxazol-4-ylethynyl)-benzoic acid methyl ester was converted to the title compound (84 mg, 88%) which was obtained as a light brown solid. MS: m/e=304.1 $[M+H]^+$.

b) N-Cyclopropylmethyl-2-(5-methyl-3-phenyl-isoxazol-4-ylethynyl)-benzamide As described for example 7b, 2-(5-methyl-3-phenyl-isoxazol-4-ylethynyl)-benzoic acid (60 mg; 0.20 mmol) instead of 3-(5-methyl-3-phenyl-isoxazol-4-ylethynyl)-benzoic acid was converted to the title compound ($SiO_2$, heptane:ethyl acetate=95:5 to 0:100, 27 mg, 38%) which was obtained as a light yellow solid. MS: m/e=357.1 $[M+H]^+$.

EXAMPLE 17

2-(5-Methyl-3-phenyl-isoxazol-4-ylethynyl)-isonicotinic acid methyl ester a) 2-Iodo-isonicotinic acid methyl ester

To a suspension of 2-iodo-isonicotinic acid (can be prepared according to J. Med. Chem. (19) 490, 1976) (24.9 g, 100 mmol) in methanol (100 mL) was added sulfuric acid (concentrated, 11 mL, 205 mmol) and the mixture was stirred at ambient temperature for 5 days followed by heating to reflux for 3 h. The reaction mixture was cooled to ambient temperature, concentrated and poured into ice cold aqueous sodium hydrogencarbonate (half-saturated) and was extracted with ethyl acetate. The combined organic layers were washed with brine, dried over sodium sulfate and concentrated. Purification by chromatography ($SiO_2$, heptane:ethyl acetate=85:15 to 80:20) afforded the title compound (20.4 mg, 77%) as a light yellow solid. MS: m/e=263.0 $[M]^+$.

b) 2-(5-Methyl-3-phenyl-isoxazol-4-ylethynyl)-isonicotinic acid methyl ester As described for example 11c, 4-ethynyl-5-methyl-3-phenyl-isoxazole (58 mg, 0.32 mmol) was converted (using 2-iodo-isonicotinic acid methyl ester instead of 2-chloro-4-iodopyridine) to the title compound (SiO$_2$, heptane:ethyl acetate=95:5 to 0:100, 70 mg, 70%) which was obtained as a light brown solid. MS: m/e=319.1 [M+H]$^+$.

EXAMPLE 18

5-Bromo-2-(5-methyl-3-phenyl-isoxazol-4-ylethynyl)-pyrimidine

As described for example 11c, 4-ethynyl-5-methyl-3-phenyl-isoxazole (55 mg, 0.30 mmol) was converted (using 5-bromo-2-iodo-pyrimidine instead of 2-chloro-4-iodopyridine) to the title compound (SiO$_2$, heptane:ethyl acetate=95:5 to 0:100, 58 mg, 56%) which was obtained as a light yellow solid. MS: m/e=341.9 [M+H]$^+$.

EXAMPLE 19

3-Methyl-6-(5-methyl-3-phenyl-isoxazol-4-ylethynyl)-pyridazine a) 3-Iodo-6-methyl-pyridazine A mixture of 3-chloro-6-methylpyridazine (2.00 g, 15.6 mmol) and hydriodic acid (57% in water, 41.1 mL, 311 mmol) was heated at reflux for 1 h. After cooling to ambient temperature aqueous sodium carbonate (saturated) was added (pH=8) and extracted with ethyl acetate (200 mL). The combined organic layers were washed with brine (60 mL), dried over sodium sulfate and concentrated afforded the title compound (2.80 mg, 82%) as a light yellow solid. MS: m/e=221.1 [M+H]$^+$.

b) 3-Methyl-6-(5-methyl-3-phenyl-isoxazol-4-ylethynyl)-pyridazine

As described for example 11c, 4-ethynyl-5-methyl-3-phenyl-isoxazole (70 mg, 0.38 mmol) was converted (using 3-iodo-6-methyl-pyridazine instead of 2-chloro-4-iodopyridine) to the title compound (SiO$_2$, heptane:ethyl acetate=95:5 to 0:100, 84 mg, 80%) which was obtained as a light brown solid. MS: m/e=276.1 [M+H]$^+$.

EXAMPLE 20

3-Chloro-2-(5-methyl-3-phenyl-isoxazol-4-ylethynyl)-pyridine

As described for example 11c, 4-ethynyl-5-methyl-3-phenyl-isoxazole (64 mg, 0.35 mmol) was converted [using 3-chloro-2-iodopyridine (prepared according to Eur. J. Org. Chem. (24), 4181, 2002) instead of 2-chloro-4-iodopyridine] to the title compound (SiO$_2$, heptane:ethyl acetate=95:5 to 0:100, 81 mg, 78%) which was obtained as a light yellow solid. MS: m/e=295.2/297.3 [M+H]$^+$.

EXAMPLE 21

5-Methyl-4-(1-methyl-1H-imidazol-2-ylethynyl)-3-phenyl-isoxazole

As described for example 11c, 4-ethynyl-5-methyl-3-phenyl-isoxazole (73 mg, 0.40 mmol) was converted (using 2-iodo-1-methyl-1H-imidazole instead of 2-chloro-4-iodopyridine) to the title compound (SiO$_2$, heptane:ethyl acetate=95:5 to 0:100, 32 mg, 30%) which was obtained as a light brown solid. MS: m/e=264.2 [M+H]$^+$.

EXAMPLE 22

5-Methyl-4-(2-methyl-3H-imidazol-4-ylethynyl)-3-phenyl-isoxazole

As described for example 11c, 4-ethynyl-5-methyl-3-phenyl-isoxazole (73 mg, 0.40 mmol) was converted using (4-iodo-2-methyl-1H-imidazole instead of 2-chloro-4-iodopyridine) to the title compound (SiO$_2$, heptane:ethyl acetate=95:5 to 0:100, 14 mg, 13%) which was obtained as a light brown solid. MS: m/e=264.2 [M+H]$^+$.

EXAMPLE 23

5-Methyl-4-(4-methyl-1H-pyrazol-3-ylethynyl)-3-phenyl-isoxazole

As described for example 11c, 4-ethynyl-5-methyl-3-phenyl-isoxazole (73 mg, 0.40 mmol) was converted [using 3-iodo-4-methyl-1H-pyrazole (prepared according to Liebigs Ann. Chem. 595, 200, 1955) instead of 2-chloro-4-iodopyridine] to the title compound (SiO$_2$, heptane:ethyl acetate=95:5 to 0:100, 56 mg, 53%) which was obtained as a light brown solid. MS: m/e=264.2 [M+H]$^+$.

EXAMPLE 24

2-Methyl-5-(5-methyl-3-phenyl-isoxazol-4-ylethynyl)-thiazole-4-carboxylic acid ethyl ester a) 5-Iodo-2-methyl-thiazole-4-carboxylic acid ethyl ester To a solution of ethyl 2-methylthiazole-4-carboxylate (11.2 g, 65.4 mmol) in acetic acid (200 mL) were added sulfuric acid (30%, 20 mL), carbontetrachloride (30 mL), iodine (33.2 g, 131 mmol) and iodic acid (11.5 g, 65.4 mmol) and the resulting reaction mixture was stirred for 19 h at 80° C. After addition of aqueous sodium thiosulfate (1 M, 500 mL) it was extracted with ethyl acetate (1000 mL). The combined organic layers were washed with aqueous sodium carbonate (saturated, 1000 mL), dried over sodium sulfate and concentrated. Purification by chromatography (SiO$_2$, heptane:ethyl acetate=95:5 to 20:80) afforded the title compound (9.00 g, 37%) as a white crystalline solid. MS: m/e=298.1 [M+H]$^+$.

b) 2-Methyl-5-(5-methyl-3-phenyl-isoxazol-4-ylethynyl)-thiazole-4-carboxylic acid ethyl ester As described for example 11c, 4-ethynyl-5-methyl-3-phenyl-isoxazole (51 mg, 0.28 mmol) was converted (using 5-iodo-2-methyl-thiazole-4-carboxylic acid ethyl ester instead of 2-chloro-4-iodopyridine) to the title compound (SiO$_2$, heptane:ethyl acetate=95:5 to 0:100, 83 mg, 84%) which was obtained as a light brown solid. MS: m/e=353.2 [M+H]$^+$.

EXAMPLE 25

4-(1H-Imidazol-2-ylethynyl)-5-methyl-3-phenyl-isoxazole

As described for example 11c, 4-ethynyl-5-methyl-3-phenyl-isoxazole (79 mg, 0.43 mmol) was converted (using 2-iodo-1H-imidazole instead of 2-chloro-4-iodopyridine) to the title compound (SiO$_2$, heptane:ethyl acetate=95:5 to 0:100, 83 mg, 77%) which was obtained as an off-white solid. MS: m/e=250.2 [M+H]$^+$.

EXAMPLE 26

2,5-Dimethyl-3-(5-methyl-3-phenyl-isoxazol-4-yl-ethynyl)-pyrazine

As described for example 11c, 4-ethynyl-5-methyl-3-phenyl-isoxazole (66 mg, 0.36 mmol) was converted [using 3-iodo-2,5-dimethyl-pyrazine (prepared from 3-chloro-2,5-dimethyl-pyrazine according to J. Med. Chem. (19) 490, 1976) instead of 2-chloro-4-iodopyridine] to the title compound (SiO$_2$, heptane:ethyl acetate=95:5 to 0:100, 89 mg, 85%) which was obtained as a white solid. MS: m/e=290.1 [M+H]$^+$.

EXAMPLE 27

N-Cyclopropylmethyl-2-(5-methyl-3-phenyl-isoxazol-4-ylethynyl)-isonicotinamide a) 2-(5-Methyl-3-phenyl-isoxazol-4-ylethynyl)-isonicotinic acid

As described for example 7a, 2-(5-methyl-3-phenyl-isoxazol-4-ylethynyl)-isonicotinic acid methyl ester (247 mg, 0.78 mmol) instead of 3-(5-methyl-3-phenyl-isoxazol-4-ylethynyl)-benzoic acid methyl ester was converted to the title compound (218 mg, 92%) which was obtained as a light brown solid. MS: m/e=305.2 [M+H]$^+$.

b) N-Cyclopropylmethyl-2-(5-methyl-3-phenyl-isoxazol-4-ylethynyl)-isonicotinamide As described for example 7b, 2-(5-methyl-3-phenyl-isoxazol-4-ylethynyl)-isonicotinic acid (50 mg; 0.16 mmol) instead of 3-(5-methyl-3-phenyl-isoxazol-4-ylethynyl)-benzoic acid was converted to the title compound (SiO$_2$, heptane:ethyl acetate=95:5 to 0:100, 26 mg, 45%) which was obtained as a yellow solid. MS: m/e=358.1 [M+H]$^+$.

EXAMPLE 28

2-(5-Methyl-3-phenyl-isoxazol-4-ylethynyl)-N-(tetrahydro-pyran-4-yl)-isonicotinamide As described for example 7b, 2-(5-methyl-3-phenyl-isoxazol-4-ylethynyl)-isonicotinic acid (50 mg; 0.16 mmol) instead of 3-(5-methyl-3-phenyl-isoxazol-4-ylethynyl)-benzoic acid was converted (using 4-amino-tetrahydropyrane instead of aminomethylcyclopropane) to the title compound (SiO$_2$, heptane:ethyl acetate=95:5 to 0:100, 46 mg, 73%) which was obtained as a yellow solid. MS: m/e=388.2 [M+H]$^+$.

EXAMPLE 29

2-(5-Methyl-3-phenyl-isoxazol-4-ylethynyl)-N-(4-methyl-thiazol-2-yl)-isonicotinamide To a solution of 2-amino-4-methylthiazole (57 mg, 0.50 mmol) in dioxane (1.2 mL) was added trimethylaluminium (2 M in heptane, 251 µl, 0.50 mmol). The resulting red-brown solution was stirred for 1 h at ambient temperature before 2-(5-methyl-3-phenyl-isoxazol-4-ylethynyl)-isonicotinic acid methyl ester (40 mg, 0.13 mmol) was added. The reaction mixture was heated for 2.25 h at 110° C. before cooling to ambient temperature. Water (29 µL) was added and the mixture was stirred for 10 min at ambient temperature. Magnesium sulfate was added and the mixture was filtered over Hyflo®. Concentration and purification by chromatography (SiO$_2$, heptane:ethyl acetate=95:5 to 0:100) was followed by separation between hydrochloric acid (1 M, 30 mL) and ethyl acetate (100 mL). The organic layers were washed with brine, dried over sodium sulfate and were concentrated affording the title compound (48 mg, 96%) as an off-white solid. MS: m/e=401.2 [M+H]$^+$.

EXAMPLE 30

2-Chloro-6-(5-methyl-3-phenyl-isoxazol-4-ylethynyl)-pyridine

As described for example 11c, 4-ethynyl-5-methyl-3-phenyl-isoxazole (92 mg, 0.50 mmol) was converted (using 2-chloro-6-iodopyridine instead of 2-chloro-4-iodopyridine) to the title compound (SiO$_2$, heptane:ethyl acetate=95:5 to 0:100, 129 mg, 87%) which was obtained as a light yellow oil. MS: m/e=295.1/297.3 [M+H]$^+$.

EXAMPLE 31

5-Methyl-2-(5-methyl-3-phenyl-isoxazol-4-ylethynyl)-pyridine

As described for example 11c, 4-ethynyl-5-methyl-3-phenyl-isoxazole (92 mg, 0.50 mmol) was converted (using 2-bromo-5-methylpyridine instead of 2-chloro-4-iodopyridine) to the title compound (SiO$_2$, heptane:ethyl acetate=95:5 to 0:100, 75 mg, 55%) which was obtained as a light brown solid. MS: m/e=275.2 [M+H]$^+$.

EXAMPLE 32

5-Methyl-4-(1-methyl-5-phenyl-1H-imidazol-2-ylethynyl)-3-phenyl-isoxazole

As described for example 11c, 4-ethynyl-5-methyl-3-phenyl-isoxazole (92 mg, 0.50 mmol) was converted [using 2-iodo-1-methyl-5-phenyl-1H-imidazole (prepared from 1-methyl-5-phenyl-1H-imidazole according to J. Org. Chem. (43) 4381, 1978) instead of 2-chloro-4-iodopyridine] to the title compound (SiO$_2$, heptane:ethyl acetate=95:5 to 0:100, 88 mg, 52%) which was obtained as a light brown solid. MS: m/e=340.2 [M+H]$^+$.

EXAMPLE 33

5-Methyl-4-(5-methyl-1-phenyl-1H-imidazol-2-yl-ethynyl)-3-phenyl-isoxazole

As described for example 11c, 4-ethynyl-5-methyl-3-phenyl-isoxazole (92 mg, 0.50 mmol) was converted [using 2-iodo-5-methyl-1-phenyl-1H-imidazole (prepared from 5-methyl-1-phenyl-1H-imidazole by reaction of 4(5)-methyl-1-phenyl-1H-imidazole with N-iodosuccinimide in N,N-dimethylformamide at ambient temperature) instead of 2-chloro-4-iodopyridine] to the title compound (SiO$_2$, heptane:ethyl acetate=95:5 to 0:100, 35 mg, 21%) which was obtained as a brown solid. MS: m/e=340.2 [M+H]$^+$.

EXAMPLE 34

2-(5-Methyl-3-phenyl-isoxazol-4-ylethynyl)-pyrazine

As described for example 11c, 4-ethynyl-5-methyl-3-phenyl-isoxazole (92 mg, 0.50 mmol) was converted (using 2-chloropyrazine instead of 2-chloro-4-iodopyridine) to the title compound (SiO$_2$, heptane:ethyl acetate=95:5 to 0:100, 78 mg, 60%) which was obtained as a light yellow solid. MS: m/e=262.1 [M+H]$^+$.

EXAMPLE 35

2-Methyl-6-(5-methyl-3-phenyl-isoxazol-4-ylethynyl)-pyridine

As described for example 11c, 4-ethynyl-5-methyl-3-phenyl-isoxazole (92 mg, 0.50 mmol) was converted (using 2-bromo-6-methylpyridine instead of 2-chloro-4-iodopyridine) to the title compound (SiO$_2$, heptane:ethyl acetate=95:5 to 0:100, 83 mg, 60%) which was obtained as a yellow oil. MS: m/e=275.2 [M+H]$^+$.

EXAMPLE 36

2-Methoxy-6-(5-methyl-3-phenyl-isoxazol-4-ylethynyl)-pyridine

As described for example 11c, 4-ethynyl-5-methyl-3-phenyl-isoxazole (92 mg, 0.50 mmol) was converted (using 2-bromo-6-methoxypyridine instead of 2-chloro-4-iodopyridine) to the title compound (SiO$_2$, heptane:ethyl acetate=95:5 to 0:100, 97 mg, 67%) which was obtained as a yellow oil. MS: m/e=291.2 [M+H]$^+$.

EXAMPLE 37

4-Methyl-2-(5-methyl-3-phenyl-isoxazol-4-ylethynyl)-pyridine

As described for example 11c, 4-ethynyl-5-methyl-3-phenyl-isoxazole (92 mg, 0.50 mmol) was converted (using 2-bromo-4-methylpyridine instead of 2-chloro-4-iodopyridine) to the title compound (SiO$_2$, heptane:ethyl acetate=95:5 to 0:100, 72 mg, 52%) which was obtained as a light brown solid. MS: m/e=275.2 [M+H]$^+$.

EXAMPLE 38

2-(5-Methyl-3-phenyl-isoxazol-4-ylethynyl)-4-trifluoromethyl-pyridine

As described for example 11c, 4-ethynyl-5-methyl-3-phenyl-isoxazole (92 mg, 0.50 mmol) was converted (using 2-bromo-4-(trifluoromethyl)pyridine instead of 2-chloro-4-iodopyridine) to the title compound (SiO$_2$, heptane:ethyl acetate=95:5 to 0:100, 124 mg, 76%) which was obtained as an off-white solid. MS: m/e=329.3 [M+H]$^+$.

EXAMPLE 39

3-Methyl-2-(5-methyl-3-phenyl-isoxazol-4-ylethynyl)-pyridine

As described for example 11c, 4-ethynyl-5-methyl-3-phenyl-isoxazole (92 mg, 0.50 mmol) was converted (using 2-bromo-3-methylpyridine instead of 2-chloro-4-iodopyridine) to the title compound (SiO$_2$, heptane:ethyl acetate=95:5 to 0:100, 91 mg, 66%) which was obtained as a light yellow solid. MS: m/e=275.2 [M+H]$^+$.

EXAMPLE 40

2-(5-Methyl-3-phenyl-isoxazol-4-ylethynyl)-6-trifluoromethyl-pyridine

As described for example 11c, 4-ethynyl-5-methyl-3-phenyl-isoxazole (92 mg, 0.50 mmol) was converted (using 2-bromo-6-(trifluoromethyl)pyridine instead of 2-chloro-4-iodopyridine) to the title compound (SiO$_2$, heptane:ethyl acetate=95:5 to 0:100, 135 mg, 82%) which was obtained as a light yellow solid. MS: m/e=329.3 [M+H]$^+$.

EXAMPLE 41

6-(5-Methyl-3-phenyl-isoxazol-4-ylethynyl)-pyridin-3-ylamine

As described for example 11c, 4-ethynyl-5-methyl-3-phenyl-isoxazole (92 mg, 0.50 mmol) was converted (using 3-amino-6-bromopyridine instead of 2-chloro-4-iodopyridine) to the title compound (SiO$_2$, heptane:ethyl acetate=95:5 to 0:100, 68 mg, 49%) which was obtained as a light brown foam. MS: m/e=276.3 [M+H]$^+$.

EXAMPLE 42

5-Chloro-2-(5-methyl-3-phenyl-isoxazol-4-ylethynyl)-pyridine

As described for example 11c, 4-ethynyl-5-methyl-3-phenyl-isoxazole (92 mg, 0.50 mmol) was converted (using 2-bromo-5-chloropyridine instead of 2-chloro-4-iodopyridine) to the title compound (SiO$_2$, heptane:ethyl acetate=95:5 to 0:100, 118 mg, 80%) which was obtained as a light yellow solid. MS: m/e=297.3 [M+H]$^+$.

EXAMPLE 43

4-(5-Methyl-3-phenyl-isoxazol-4-ylethynyl)-benzenesulfonamide

As described for example 11c, 4-ethynyl-5-methyl-3-phenyl-isoxazole (92 mg, 0.50 mmol) was converted (using 4-iodobenzenesulphonamide instead of 2-chloro-4-iodopyridine) to the title compound (SiO$_2$, heptane:ethyl acetate=95:5 to 0:100, 120 mg, 71%) which was obtained as a white solid. MS: m/e=339.2 [M+H]$^+$.

EXAMPLE 44

4-Ethyl-2-(5-methyl-3-phenyl-isoxazol-4-ylethynyl)-pyridine

As described for example 11c, 4-ethynyl-5-methyl-3-phenyl-isoxazole (92 mg, 0.50 mmol) was converted (using 2-bromo-4-ethylpyridine instead of 2-chloro-4-iodopyridine) to the title compound (SiO$_2$, heptane:ethyl acetate=95:5 to 0:100, 74 mg, 51%) which was obtained as a yellow oil. MS: m/e=289.1 [M+H]$^+$.

EXAMPLE 45

2-(5-Methyl-3-phenyl-isoxazol-4-ylethynyl)-quinoxaline

As described for example 11c, 4-ethynyl-5-methyl-3-phenyl-isoxazole (92 mg, 0.50 mmol) was converted (using 2-chloroquinoxaline instead of 2-chloro-4-iodopyridine) to the title compound (SiO$_2$, heptane:ethyl acetate=95:5 to 0:100, 118 mg, 76%) which was obtained as a light yellow solid. MS: m/e=312.2 [M+H]$^+$.

EXAMPLE 46

6-(5-Methyl-3-phenyl-isoxazol-4-ylethynyl)-pyrazin-2-ylamine

As described for example 11c, 4-ethynyl-5-methyl-3-phenyl-isoxazole (92 mg, 0.50 mmol) was converted (using 2-amino-6-chloropyrazine instead of 2-chloro-4-iodopyridine) to the title compound (SiO$_2$, heptane:ethyl acetate=95:5 to 0:100, 47 mg, 34%) which was obtained as a brown solid. MS: m/e=277.2 [M+H]$^+$.

EXAMPLE 47

5-(5-Methyl-3-phenyl-isoxazol-4-ylethynyl)-pyrazin-2-ylamine

As described for example 11c, 4-ethynyl-5-methyl-3-phenyl-isoxazole (92 mg, 0.50 mmol) was converted (using 2-amino-5-bromopyrazine instead of 2-chloro-4-iodopyridine) to the title compound (SiO$_2$, heptane:ethyl acetate=95:5 to 0:100, 35 mg, 25%) which was obtained as a brown solid. MS: m/e=277.2 [M+H]$^+$.

EXAMPLE 48

2-(5-Methyl-3-phenyl-isoxazol-4-ylethynyl)-pyrimidine

As described for example 11c, 4-ethynyl-5-methyl-3-phenyl-isoxazole (92 mg, 0.50 mmol) was converted (using 2-chloropyrimidine instead of 2-chloro-4-iodopyridine) to the title compound (SiO$_2$, heptane:ethyl acetate=95:5 to 0:100, 42 mg, 32%) which was obtained as a brown solid. MS: m/e=262.2 [M+H]$^+$.

EXAMPLE 49

5-Ethyl-2-(5-methyl-3-phenyl-isoxazol-4-ylethynyl)-pyrimidine

As described for example 11c, 4-ethynyl-5-methyl-3-phenyl-isoxazole (92 mg, 0.50 mmol) was converted (using 2-chloro-5-ethylpyrimidine instead of 2-chloro-4-iodopyridine) to the title compound (SiO$_2$, heptane:ethyl acetate=95:5 to 0:100, 40 mg, 28%) which was obtained as a brown oil. MS: m/e=290.1 [M+H]$^+$.

EXAMPLE 50

3,5-Dimethyl-2-(5-methyl-3-phenyl-isoxazol-4-ylethynyl)-3H-imidazole-4-carboxylic acid ethyl ester As described for example 11c, 4-ethynyl-5-methyl-3-phenyl-isoxazole (92 mg, 0.50 mmol) was converted (using 2-bromo-3,5-dimethyl-3H-imidazole-4-carboxylic acid ethyl ester instead of 2-chloro-4-iodopyridine) to the title compound (SiO$_2$, heptane:ethyl acetate=95:5 to 0:100, 110 mg, 63%) which was obtained as a light yellow solid. MS: m/e=350.3 [M+H]$^+$.

EXAMPLE 51

3-(5-Methyl-3-phenyl-isoxazol-4-ylethynyl)-4H-5-oxa-2,9b-diaza-cyclopenta[a]naphthalene a) 3-Trimethylsilanylethynyl-4H-5-oxa-2,9b-diaza-cyclopenta[a]naphthalene As described for example 3a, 3-iodo-4H-5-oxa-2,9b-diaza-cyclopenta[a]naphthalene (may be prepared in analogy to WO2002046166, 3.00 g, 10.1 mmol) instead of 2-amino-5-bromopyridine was converted to the title compound (SiO$_2$, heptane:ethyl acetate=100:0 to 40:60, 1.74 g, 64%) which was obtained as a light brown oil. MS: m/e=269.5 [M+H]$^+$.

b) 3-Ethynyl-4H-5-oxa-2,9b-diaza-cyclopenta[a]naphthalene

As described for example 3b, 3-trimethylsilanylethynyl-4H-5-oxa-2,9b-diaza-cyclopenta[a]naphthalene (1.72 g, 6.41 mmol) instead of 5-trimethylsilanylethynyl-pyridin-2-ylamine was converted to the title compound (1.20 g, 95%) which was obtained as a light brown solid. MS: m/e=197.9 [M+H]$^+$.

c) 3-(5-Methyl-3-phenyl-isoxazol-4-ylethynyl)-4H-5-oxa-2,9b-diaza-cyclopenta[a]naphthalene As described for example 1,4-iodo-5-methyl-3-phenyl-isoxazole (112 mg, 0.39 mmol) was converted (using 3-ethynyl-4H-5-oxa-2,9b-diaza-cyclopenta[a]naphthalene instead of 2-ethynylpyridine) to the title compound (SiO$_2$, heptane:ethyl acetate=95:5 to 0:100, 60 mg, 44%) which was obtained as a light brown solid. MS: m/e=354.2 [M+H]$^+$.

EXAMPLE 52

3-Methyl-2-(5-methyl-3-phenyl-isoxazol-4-ylethynyl)-5,6,7,8-tetrahydro-imidazo[1,2-a]pyridine a) 1-Ethyl-4-iodo-5-methyl-2-propyl-1H-imidazole To a solution of 3-methyl-5,6,7,8-tetrahydro-imidazo[1,2-a]pyridine (Eur. J. Med. Chem. 10(5), 528, 1975; 1.85 g, 13.6 mmol) in acetic acid (50 mL) was added N-iodsuccinimide (4.28 g, 19.0 mmol) and the reaction mixture was stirred for 3 h at ambient temperature. It was concentrated and the residue extracted with aqueous sodium carbonate (sat.) and ethyl acetate. The combined organic layers were dried over sodium sulfate and concentrated. Purification by chromatography (SiO$_2$, dichloromethane:methanol=100:0 to 93:7) afforded the title compound (3.00 g, 84%) as a dark brown solid. MS: m/e=262.0 [M]$^+$.

b) 2-Ethynyl-3-methyl-5,6,7,8-tetrahydro-imidazo[1,2-a]pyridine

As described for example 3a, 1-ethyl-4-iodo-5-methyl-2-propyl-1H-imidazole (2.60 g, 9.92 mmol) instead of 2-amino-5-bromopyridine was converted to 3-methyl-2-trimethylsilanyl-ethynyl-5,6,7,8-tetrahydro-imidazo[1,2-a]pyridine (SiO$_2$, dichloromethane:methanol=100:0 to 98:2, 890 mg, 39%) which was obtained as a dark brown semisolid and used further without detailed characterization. As described for example 3b, 3-methyl-2-trimethylsilanylethynyl-5,6,7,8-tetrahydro-imidazo[1,2-a]pyridine (890 g, 3.83 mmol) instead of 5-trimethylsilanyl-ethynyl-pyridin-2-ylamine was converted to the title compound (SiO$_2$, ethyl acetate, 310 mg, 51%) which was obtained as a light brown solid. MS: m/e=161.3 [M+H]$^+$.

c) 3-Methyl-2-(5-methyl-3-phenyl-isoxazol-4-yl-ethynyl)-5,6,7,8-tetrahydro-imidazo[1,2-a]pyridine As described for example 1,4-iodo-5-methyl-3-phenyl-isoxazole (137 mg, 0.48 mmol) was converted (using 2-ethynyl-3-methyl-5,6,7,8-tetrahydro-imidazo[1,2-a]pyridine instead of 2-ethynylpyridine) to the title compound (SiO$_2$, heptane:ethyl acetate=95:5 to 0:100, 54 mg, 35%) which was obtained as a light brown solid. MS: m/e=318.2 [M+H]$^+$.

EXAMPLE 53

4-[5-(4-Fluoro-phenyl)-1-methyl-1H-pyrazol-3-yl-ethynyl]-5-methyl-3-phenyl-isoxazole a) 3-Ethynyl-5-(4-fluoro-phenyl)-1-methyl-1H-pyrazole To a solution of (1-diazo-2-oxo-propyl)-phosphonic acid dimethyl ester (2.27 g, 11.8 mmol) in methanol (100 mL) were added 5-(4-fluoro-phenyl)-1-methyl-1H-pyrazole-3-carbaldehyde (may be prepared in analogy to WO2005014553, 2.00 g, 9.8 mmol) and potassium carbonate (2.84 g, 20.56 mmol) and the resulting yellow suspension was stirred for 19 h at ambient temperature. After extraction with aqueous sodium hydrogencarbonate and ethyl acetate the combined organic layers were washed with brine, dried over sodium sulfate. Concentration and purification by chromatography (SiO$_2$, hexane:ethyl acetate=100:0 to 75:25) afforded the title compound (1.83 g, 93%) as a white solid. MS: m/e=201.3 [M+H]$^+$.

b) 4-[5-(4-Fluoro-phenyl)-1-methyl-1H-pyrazol-3-ylethynyl]-5-methyl-3-phenyl-isoxazole As described for example 1,4-iodo-5-methyl-3-phenyl-isoxazole (108 mg, 0.38 mmol) was converted (using 3-ethynyl-5-(4-fluoro-phenyl)-1-methyl-1H-pyrazole instead of 2-ethynylpyridine) to the title compound (SiO$_2$, heptane:ethyl acetate=95:5 to 0:100, 44 mg, 32%) which was obtained as a yellow solid. MS: m/e=358.1 [M+H]$^+$.

EXAMPLE 54

1-(4-Fluoro-phenyl)-5-methyl-3-(5-methyl-3-phenyl-isoxazol-4-ylethynyl)-1H-[1,2,4]triazole a) [1-(4-Fluoro-phenyl)-5-methyl-1H-[1,2,4]triazol-3-yl]-methanol To a suspension of 1-(4-fluoro-phenyl)-5-methyl-1H-[1,2,4]triazole-3-carboxylic acid (may be prepared in analogy to DE3525205, 1986, 10.7 g, 48.4 mmol) in THF (50 mL) was added borane (1 M in THF, 121 mL, 121 mmol) and the resulting suspension was heated to reflux for 1 h. After concentration and extraction with aqueous sodium hydrogencarbonate and ethyl acetate the combined organic layers were washed with brine and dried over sodium sulfate. Concentration and purification by chromatography (SiO$_2$, hexane:ethyl acetate=100:0 to 33:67) afforded the title compound (4.60 g, 46%) as a white solid. MS: m/e=208.4 [M+H]$^+$.

b) 1-(4-Fluoro-phenyl)-5-methyl-1H-[1,2,4]triazole-3-carbaldehyde

A suspension of [1-(4-fluoro-phenyl)-5-methyl-1H-[1,2,4]triazol-3-yl]-methanol (2.20 g, 10.6 mmol) and manganese (IV) oxide (10.3 g, 106 mmol) in dichloromethane (110 mL) was heated at reflux for 1 h. After cooling to ambient temperature it was filtered and concentrated affording the title compound (1.80 g, 33%) as a light yellow solid. MS: m/e=206.3 [M+H]$^+$.

c) 3-Ethynyl-1-(4-fluoro-phenyl)-5-methyl-1H-[1,2,4]triazole

As described for example 53a, 1-(4-Fluoro-phenyl)-5-methyl-1H-[1,2,4]triazole-3-carbaldehyde (1.00 mg, 4.88 mmol) instead of 5-(4-fluoro-phenyl)-1-methyl-1H-pyrazole-3-carbaldehyde was converted to the title compound (25 mg, 6%) which was obtained as a light yellow oil. MS: m/e=202.3 [M+H]$^+$.

d) 1-(4-Fluoro-phenyl)-5-methyl-3-(5-methyl-3-phenyl-isoxazol-4-ylethynyl)-1H-[1,2,4]triazole As described for example 1,4-iodo-5-methyl-3-phenyl-isoxazole (108 mg, 0.38 mmol) was converted (using 3-ethynyl-1-(4-fluoro-phenyl)-5-methyl-1H-[1,2,4]triazole instead of 2-ethynylpyridine) to the title compound (SiO$_2$, heptane:ethyl acetate=95:5 to 0:100, 22 mg, 16%) which was obtained as a light brown solid. MS: m/e=359.1 [M+H]$^+$.

EXAMPLE 55

4-[5-(3-Fluoro-phenyl)-1-methyl-1H-pyrazol-3-yl-ethynyl]-5-methyl-3-phenyl-isoxazole a) 3-Ethynyl-5-(3-fluoro-phenyl)-1-methyl-1H-pyrazole As described for example 53a, 5-(3-fluoro-phenyl)-1-methyl-1H-pyrazole-3-carbaldehyde (may be prepared in analogy to WO2005014553, 515 mg, 2.52 mmol) instead of 5-(4-fluoro-phenyl)-1-methyl-1H-pyrazole-3-carbaldehyde was converted to the title compound (500 mg, 99%) which was obtained as a light yellow oil. MS: m/e=201.1 [M+H]$^+$.

b) 4-[5-(3-Fluoro-phenyl)-1-methyl-1H-pyrazol-3-ylethynyl]-5-methyl-3-phenyl-isoxazole As described for example 1,4-iodo-5-methyl-3-phenyl-isoxazole (108 mg, 0.38 mmol) was converted (using 3-ethynyl-5-(3-fluoro-phenyl)-1-methyl-1H-pyrazole instead of 2-ethynylpyridine) to the title compound (SiO$_2$, heptane: ethyl acetate=95:5 to 0:100, 48 mg, 35%) which was obtained as a light yellow oil. MS: m/e=358.1 [M+H]$^+$.

EXAMPLE 56

4-[1-(3,5-Difluoro-phenyl)-2,5-dimethyl-1H-imidazol-4-ylethynyl]-5-methyl-3-phenyl-isoxazole As described for example 1,4-iodo-5-methyl-3-phenyl-isoxazole (94 mg, 0.33 mmol) was converted [using 1-(3,5-difluoro-phenyl)-4-ethynyl-2,5-dimethyl-1H-imidazole (may be prepared in analogy to WO2005118568) instead of 2-ethynylpyridine] to the title compound (SiO$_2$, heptane: ethyl acetate=95:5 to 0:100, 41 mg, 32%) which was obtained as an off-white solid. MS: m/e=390.2 [M+H]$^+$.

EXAMPLE 57

4-[1-(4-Fluoro-phenyl)-2,5-dimethyl-1H-imidazol-4-ylethynyl]-5-methyl-3-phenyl-isoxazole As described for example 1,4-iodo-5-methyl-3-phenyl-isoxazole (100 mg, 0.38 mmol) was converted [using 4-ethynyl-1-(4-fluoro-phenyl)-2,5-dimethyl-1H-imidazole (may be prepared in analogy to WO2005118568) instead of 2-ethynylpyridine] to the title compound (SiO$_2$, heptane:ethyl acetate=95:5 to 0:100, 48 mg, 37%) which was obtained as an off-white solid. MS: m/e=372.2 [M+H]$^+$.

EXAMPLE 58

2-[3-(3-Chloro-4-methoxy-phenyl)-5-methyl-isoxazol-4-ylethynyl]-pyridine

As described for example 11c, 3-(3-chloro-4-methoxy-phenyl)-4-ethynyl-5-methyl-isoxazole (134 mg, 0.50 mmol) instead of 4-ethynyl-5-methyl-3-phenyl-isoxazole was converted (using 2-bromopyridine instead of 2-chloro-4-iodopyridine) to the title compound (SiO$_2$, heptane:ethyl acetate=95:5 to 0:100, 117 mg, 72%) which was obtained as a white solid. MS: m/e=325.2 [M+H]$^+$.

EXAMPLE 59

2-[3-(4-Chloro-phenyl)-5-methyl-isoxazol-4-ylethynyl]-pyridine

As described for example 11c, 3-(4-chloro-phenyl)-4-ethynyl-5-methyl-isoxazole (109 mg, 0.50 mmol) instead of 4-ethynyl-5-methyl-3-phenyl-isoxazole was converted (using 2-bromopyridine instead of 2-chloro-4-iodopyridine) to the title compound (SiO$_2$, heptane:ethyl acetate=95:5 to 0:100, 129 mg, 87%) which was obtained as a light brown solid. MS: m/e=295.1 [M+H]$^+$.

EXAMPLE 60

2-(5-Methyl-3-phenyl-isoxazol-4-ylethynyl)-thiazole-5-carboxylic acid methyl ester As described for example 11c, 4-ethynyl-5-methyl-3-phenyl-isoxazole (92 mg, 0.50 mmol) was converted (using methyl 2-bromothiazole-5-carboxylate instead of 2-chloro-4-iodopyridine) to the title compound (SiO$_2$, heptane:ethyl acetate=95:5 to 0:100, 139 mg, 86%) which was obtained as a light yellow solid. MS: m/e=325.2 [M+H]$^+$.

EXAMPLE 61

2-(5-Methyl-3-phenyl-isoxazol-4-ylethynyl)-thiazole-4-carboxylic acid methyl ester As described for example 11c, 4-ethynyl-5-methyl-3-phenyl-isoxazole (92 mg, 0.50 mmol) was converted (using methyl 2-bromothiazole-4-carboxylate instead of 2-chloro-4-iodopyridine) to the title compound (SiO$_2$, heptane:ethyl acetate=95:5 to 0:100, 113 mg, 70%) which was obtained as a light yellow solid. MS: m/e=325.2 [M+H]$^+$.

EXAMPLE 62

4-(2-Isopropyl-thiazol-4-ylethynyl)-5-methyl-3-phenyl-isoxazole

As described for example 11c, 4-ethynyl-5-methyl-3-phenyl-isoxazole (92 mg, 0.50 mmol) was converted (using 4-bromo-2-isopropylthiazole instead of 2-chloro-4-iodopyridine) to the title compound (SiO$_2$, heptane:ethyl acetate=95:5 to 0:100, 23 mg, 15%) which was obtained as a yellow oil. MS: m/e=309.3 [M+H]$^+$.

The invention claimed is:

1. An aryl-4-ethynyl-isoxazole derivative of formula I

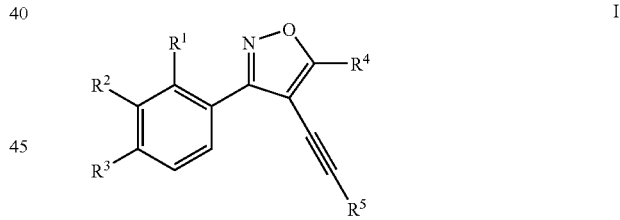

wherein $R^1$, $R^2$, and $R^3$ are each independently hydrogen, lower alkyl, halogen, lower alkoxy or amino;

$R^4$ is lower alkyl;

$R^5$ is optionally substituted aryl or heteroaryl, wherein the substituents are selected from the group consisting of lower alkyl, lower alkoxy, CF$_3$, halogen, hydroxy, amino, —(CH$_2$)$_n$—CN, —C(O)O-lower alkyl, —S(O)$_2$NH$_2$, —C(O)—NH—(CH$_2$)$_n$-cycloalkyl, —C(O)—NH-heterocyclyl, —C(O)—NH-heteroaryl, and optionally substituted aryl, wherein the substituents are selected from halogen;

n is 0 or 1;

or a pharmaceutically acceptable acid addition salt thereof.

2. A compound of claim 1, in which $R^1$, $R^2$ and $R^3$ are hydrogen.

3. A compound of claim 1, in which $R^1$, $R^2$, and $R^3$ are each independently hydrogen, halogen or lower alkoxy.

4. A compound of claim 3, in which R$^1$ is hydrogen, R$^2$ is hydrogen or halogen, and R$^3$ is hydrogen, halogen, or alkoxy.

5. A compound of claim 3 wherein R$^2$ is halogen.

6. A compound of claim 5, wherein R$^2$ is chloro.

7. A compound of claim 3, wherein R$^3$ is alkoxy.

8. A compound of claim 7, wherein R$^3$ is methoxy.

9. A compound of claim 1, wherein R$^5$ is optionally substituted aryl or heteroaryl, wherein the substituents are selected from the groups consisting of lower alkyl, lower alkoxy, CF$_3$, halogen, hydroxy, amino, CN, —CH$_2$CN, —C(O)O-lower alkyl, —S(O)$_2$NH$_2$, —C(O)—NH—CH$_2$-cycloalkyl, —C(O)—NH-heterocyclyl, —C(O)—NH-heteroaryl, optionally substituted aryl, wherein the substituents are selected from halogen.

10. A compound of claim 9, wherein R$^5$ is optionally substituted pyridinyl.

11. A compound of claim 10, wherein the compound is selected from the group consisting of
2-(5-methyl-3-phenyl-isoxazol-4-ylethynyl)-pyridine,
2-(5-methyl-3-phenyl-isoxazol-4-ylethynyl)-isonicotinic acid methyl ester,
N-cyclopropylmethyl-2-(5-methyl-3-phenyl-isoxazol-4-ylethynyl)-isonicotinamide,
2-(5-methyl-3-phenyl-isoxazol-4-ylethynyl)-N-(tetrahydro-pyran-4-yl)-isonicotinamide,
2-(5-methyl-3-phenyl-isoxazol-4-ylethynyl)-N-(4-methyl-thiazol-2-yl)-isonicotinamide,
2-chloro-6-(5-methyl-3-phenyl-isoxazol-4-ylethynyl)-pyridine,
5-methyl-2-(5-methyl-3-phenyl-isoxazol-4-ylethynyl)-pyridine,
2-methyl-6-(5-methyl-3-phenyl-isoxazol-4-ylethynyl)-pyridine,
4-methyl-2-(5-methyl-3-phenyl-isoxazol-4-ylethynyl)-pyridine,
2-(5-methyl-3-phenyl-isoxazol-4-ylethynyl)-4-trifluoromethyl-pyridine,
3-methyl-2-(5-methyl-3-phenyl-isoxazol-4-ylethynyl)-pyridine,
6-(5-methyl-3-phenyl-isoxazol-4-ylethynyl)-pyridin-3-ylamine,
5-chloro-2-(5-methyl-3-phenyl-isoxazol-4-ylethynyl)-pyridine,
4-ethyl-2-(5-methyl-3-phenyl-isoxazol-4-ylethynyl)-pyridine, and
2-[3-(4-chloro-phenyl)-5-methyl-isoxazol-4-ylethynyl]-pyridine.

12. A compound of claim 9, wherein R$^5$ is optionally substituted phenyl.

13. A compound of claim 12, which compound is selected from the group consisting of
3-(5-methyl-3-phenyl-isoxazol-4-ylethynyl)-N-(tetrahydro-pyran-4-yl)-benzamide,
2-(5-methyl-3-phenyl-isoxazol-4-ylethynyl)-benzoic acid methyl ester and
2-(5-methyl-3-phenyl-isoxazol-4-ylethynyl)-phenylamine.

14. A compound of claim 9, wherein R$^5$ is optionally substituted pyridazine.

15. A compound of claim 14, which compound is
3-methyl-6-(5-methyl-3-phenyl-isoxazol-4-ylethynyl)-pyridazine.

16. A compound of claim 9, wherein R$^5$ is optionally substituted imidazole.

17. A compound of claim 16, wherein the compound is selected from the group consisting of 5-methyl-4-(1-methyl-1H-imidazol-2-ylethynyl)-3-phenyl-isoxazole,
5-methyl-4-(2-methyl-3H-imidazol-4-ylethynyl)-3-phenyl-isoxazole,
4-(1H-imidazol-2-ylethynyl)-5-methyl-3-phenyl-isoxazole,
5-methyl-4-(1-methyl-5-phenyl-1H-imidazol-2-ylethynyl)-3-phenyl-isoxazole,
5-methyl-4-(5-methyl-1-phenyl-1H-imidazol-2-ylethynyl)-3-phenyl-isoxazole,
3,5-dimethyl-2-(5-methyl-3-phenyl-isoxazol-4-ylethynyl)-3H-imidazole-4-carboxylic acid ethyl ester,
4-[1-(3,5-difluoro-phenyl)-2,5-dimethyl-1H-imidazol-4-ylethynyl]-5-methyl-3-phenyl-isoxazole and
4-[1-(4-fluoro-phenyl)-2,5-dimethyl-1H-imidazol-4-ylethynyl]-5-methyl-3-phenyl-isoxazole.

18. A compound of claim 9, wherein R$^5$ is optionally substituted pyrazole.

19. A compound of claim 18, which compound is selected from the group consisting of
5-methyl-4-(4-methyl-1H-pyrazol-3-ylethynyl)-3-phenyl-isoxazole,
4-[5-(4-fluoro-phenyl)-1-methyl-1H-pyrazol-3-ylethynyl]-5-methyl-3-phenyl-isoxazole and
4-[5-(3-fluoro-phenyl)-1-methyl-1H-pyrazol-3-ylethynyl]-5-methyl-3-phenyl-isoxazole.

20. A compound of claim 9, wherein R$^5$ is optionally substituted thiazole.

21. A compound of claim 20, which compound is selected from the group consisting of
2-methyl-5-(5-methyl-3-phenyl-isoxazol-4-ylethynyl)-thiazole-4-carboxylic acid ethyl ester,
2-(5-methyl-3-phenyl-isoxazol-4-ylethynyl)-thiazole-5-carboxylic acid methyl ester, and
2-(5-methyl-3-phenyl-isoxazol-4-ylethynyl)-thiazole-4-carboxylic acid methyl ester.

22. A compound of claim 9, wherein R$^5$ is optionally substituted pyrazine.

23. A compound of claim 22, wherein the compound is selected from the group consisting of
2,5-dimethyl-3-(5-methyl-3-phenyl-isoxazol-4-ylethynyl)-pyrazine,
2-(5-methyl-3-phenyl-isoxazol-4-ylethynyl)-pyrazine,
6-(5-methyl-3-phenyl-isoxazol-4-ylethynyl)-pyrazin-2-ylamine and
5-(5-methyl-3-phenyl-isoxazol-4-ylethynyl)-pyrazin-2-ylamine.

24. A compound of claim 9, wherein R$^5$ is optionally substituted quinoxaline.

25. A compound of claim 24, wherein the compound is
2-(5-methyl-3-phenyl-isoxazol-4-ylethynyl)-quinoxaline.

26. A compound of claim 9, wherein R$^5$ is optionally substituted 5,5,7,8-tetrahydro-imidazo[1,2-a]pyridine.

27. A compound of claim 26, wherein the compound is
3-methyl-2-(5-methyl-3-phenyl-isoxazol-4-ylethynyl)-5,6,7,8-tetrahydro-imidazo[1,2-a]pyridine.

28. A pharmaceutical composition comprising an aryl-4-ethynyl-isoxazole derivative of formula I

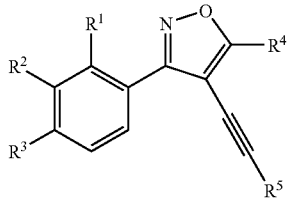

wherein

R¹, R², and R³ are each independently hydrogen, lower alkyl, halogen, lower alkoxy or amino;

R⁴ is lower alkyl;

R⁵ is optionally substituted aryl or heteroaryl, wherein the substituents are selected from the group consisting of lower alkyl, lower alkoxy, CF₃, halogen, hydroxy, amino, —(CH₂)$_n$—CN, —C(O)O-lower alkyl, —S(O)₂NH₂, —C(O)—NH—(CH₂)$_n$-cycloalkyl, —C(O)—NH-heterocyclyl, —C(O)—NH-heteroaryl, and optionally substituted aryl, wherein the substituents are selected from halogen;

n is 0 or 1;

or a pharmaceutically acceptable acid addition salt thereof and a pharmaceutically acceptable carrier.

* * * * *